US007507800B2

(12) United States Patent
van Ommen et al.

(10) Patent No.: US 7,507,800 B2
(45) Date of Patent: *Mar. 24, 2009

(54) DIAGNOSTIC TEST KIT FOR DETERMINING A PREDISPOSITION FOR BREAST AND OVARIAN CANCER, MATERIALS AND METHODS FOR SUCH DETERMINATION

(75) Inventors: Garrit-Jan Boudewijn van Ommen, Amsterdam (NL); Anne Petrij-Bos, Leiden (NL); Egbert Bakker, Leiden (NL); Peter Devilee, Leiden (NL)

(73) Assignee: Rijksuniversiteit te Leiden, Leiden (NL)

( * ) Notice: Subject to any disclaimer, the term of this patent is extended or adjusted under 35 U.S.C. 154(b) by 149 days.

This patent is subject to a terminal disclaimer.

(21) Appl. No.: 10/654,382

(22) Filed: Sep. 3, 2003

(65) Prior Publication Data

US 2005/0019782 A1 Jan. 27, 2005

Related U.S. Application Data

(63) Continuation of application No. 09/445,174, filed as application No. PCT/NL98/00325 on Jun. 3, 1998, now Pat. No. 6,733,966.

(30) Foreign Application Priority Data

Jun. 4, 1997 (EP) .................................. 97201700

(51) Int. Cl.
*C07H 21/00* (2006.01)
*C12Q 1/68* (2006.01)
(52) U.S. Cl. .......................................... 536/22.1; 435/6
(58) Field of Classification Search .............. 536/24.31, 536/22.1, 24.33; 435/6
See application file for complete search history.

(56) References Cited

U.S. PATENT DOCUMENTS

| 5,622,829 | A | 4/1997 | King et al. |
| 5,756,294 | A | 5/1998 | White et al. |
| 6,150,514 | A | 11/2000 | Swensen |
| 6,733,966 | B1 * | 5/2004 | van Ommen et al. ............ 435/6 |

FOREIGN PATENT DOCUMENTS

EP 0699754 A1 6/1996
EP 0705903 A1 10/1996
WO WO94/21791 9/1994

OTHER PUBLICATIONS

Nadine Puget, Delphine Torchard, Olga M. Serova-Sinilnikova, Henry T. Lynch, Jean Feunteun, Gilbert M. Lenoir, and Sylvie Mazoyer, "A 1-kb Alu-mediated Germ-Line Deletion Removing BRCA1 Exon 17," *Cancer Research* (1997) 57: 828-831.
Anne Petrij-Bosch, Tamara Peelen, Margreethe van Vliet, Ronald van Eijk, Renske Olmer, Marion Drüsedau, Frans B.L. Hogervorst, Sandra Hageman, Petronella J.W. Arts, Marjolijn J.L. Ligtenberg, Hanne Meijers-Heijboer, Jan G.M. Klijn, Hans F.A. Vasen, Cees J. Cornelisse, Laura J. van't Veer, Egbert Bakker, Gert-Jan B. van Ommen and Peter Devilee, "BRCA1 genomic deletions are major founder mutations in Dutch breast cancer patients," *Nature Genetics* (1997) 17: 341-345. Note: Erratum in *Nature Genetics* (1997) 17: 503.
Todd M. Smith, Ming K. Lee, Csilla I. Szabo, Nicole Jerome, Mark McEuen, Matthew Taylor, Leroy Hood, and Mary-Claire King, "Complete Genomic Sequence and Analysis of 117 kb of Human DNA Containing the Gene BRCA1," *Genome Research* (1996) 6: 1029-1049.
Fergus J. Couch, Barbara L. Weber, and the Breast Cancer Information Core, "Mutations and Polymorphisms in the Familial Early-Onset Breast Cancer (*BRCA1*) Gene," *Human Mutation* (1996) 8: 8-18.
Niels S. Rüdiger, Niels Gregersen and Morten C. Kielland-Brandt, "One short well conserved region of *Alu*-sequences is involved in human gene rearrangements and has homology with prokaryotic chi," *Nucleic Acids Research* (1995) 23: 256-260.
Miki et al., "A strong candidate for the breast and ovarian cancer susceptibility gene BRCA1", *Science*, (1994) 266: 66-71.

* cited by examiner

*Primary Examiner*—Suryaprabha Chunduru
(74) *Attorney, Agent, or Firm*—Hoffmann & Baron, LLP (57) ABSTRACT

The present invention relates generally to the field of human genetics, and more specifically to the detection of a specific type of germline mutations in the BRCA1 gene, which will predispose to breast and ovarian cancer. In addition, the invention relates to the molecular genetic mechanism that may have mediated the genesis of these mutations, in particular the role of Alu repetitive DNA elements present in the intronic regions of BRCA1. The invention further relates to somatic mutations of this type in the BRCA1 gene in human breast and ovarian cancer, and their use in the diagnosis and prognosis of human breast and ovarian cancer. The invention more particularly relates to the screening of this type of BRCA1 mutations in human genomic DNA, which are useful for the diagnosis of inherited predisposition to breast and ovarian cancer.

7 Claims, 4 Drawing Sheets

Figure 1

```
79441  agaggtcttg ctataagcct tcatccggag agtgtaggt  agaggcctg  ggttaagtat
                 Start deletion
79501  gcagattact gcagtgattt tacatctaaa tgtccatttt agATCAACTG GAATGGATGG
79561  TACAGCTGTG TGGTGCTTCT GTGGTGAAGG AGCTTTCATC ATTCACCCTT GGCACAgtaa
79621  gtattgggtg ccctgtcaga gaggaggac  acaatattct ctcctgtgag caagactggc
79681  acctgtcagt ccctatggat gccctactg  tagcctcaga agtcttctct gcccacatac
79741  ctgtgccaaa agactccatc tgtaagggat gggtaaggat ttgagaactg cacatattaa
79801  atatactgag ggaagacttt ttccctctaa ctcttttcc  catatgtccc tccccctcct
79861  ctctgtgact gccccagcat actgtgtttc aacaaatcat caagaaatga tgggctggag
79921  gctgggcatg gtggctcatg tctgtaatcc cagcactttg ggaggccgag gcaggtggat
                             End deletion
79981  cacttgtcag gagtttgaga ccagcctggc caacatggtg aaacccccatc tgtactaaaa
80041  aaaaaaaaac aaaaagtagc caggcctggt ggagcatgc  tgtaatgcca gctatttggg
80101  aagttgaggt gtgagcatcg cttgaacgtg ggaggcagag gttgcagtga gccaagattg
```

(SEQ. ID. NO.: 20)

```
44423  cctgtaatcc cagcactttg ggaggccgag gcgggaggat catgtg..gt caggagatcc
       |||||||||| ||| ||| || ||||||| || ||| |       ||| ||  || |||| ||
48256  cctgtaaccc cagcactttg ggaggccaag gcaggcgaat gcaggcgaat cacctgaggt cgggagctcg 44481  agaccatcct ggctaacacg gtgaaacacc att tctacta aaatacaaa aaattagctg
       |||||||||| |||||||||| |||||||||| ||| ||||||| ||| |||||| ||||||||
Jnctn  agaccatcct ggctaacacg gtgaaacacc att tctacta aaactacaaa aaattagccg
       |||||||||| |||||||||| |||||||||| ||| ||||||| |||||||||| ||||||||
48316  agaccagcct gaccaacatg gagaaaccac atc tctacta aaactacaaa aaattagccg 44541  ggcatggtgg cgggcgcctg taatcccagc tactcaggag gctgaagcag aagaatggct
       ||| || ||| ||  |  ||| |||||||||| |||| ||||| |          |
48376  ggcgtggtgg cacatgcctg taatcccagc tacttgggag ctacggtgcc tggcctagtt
```

(SEQ. ID. NO.: 21)

(SEQ. ID. NO.: 22)

Figure 4

DIAGNOSTIC TEST KIT FOR DETERMINING A PREDISPOSITION FOR BREAST AND OVARIAN CANCER, MATERIALS AND METHODS FOR SUCH DETERMINATION

This application is a continuation of U.S. application Ser. No. 09/445,174 filed on Apr. 24, 2000, now U.S. Pat. No. 6,733,966. The specification of U.S. application Ser. No. 09/445,174 is hereby incorporated by reference.

This application asserts priority of international application numbers PCT/NL98/00325, filed on Jun. 3, 1998, and EP97201700.8, filed on Jun. 4, 1997. The specifications of PCT/NL98/00325 and EP97201700.8 are hereby incorporated by reference.

The present invention relates generally to the field of human genetics. In particular the invention relates to methods and means (diagnostic test kits) for studying the predisposition for certain types of cancers often having a hereditary component and more specifically to the detection of a specific type of germline mutations in genes involved or associated with certain types of hereditary cancers, in particular the (human) BRCA1 gene, which will predispose to breast and ovarian cancer. In addition, the invention reveals a molecular genetic mechanism that may have mediated the genesis of these mutations, in particular the role of Alu repetitive DNA elements present in the intronic regions of BRCA1. The invention further relates to somatic mutations of this type in the BRCA1 gene in human breast and ovarian cancer, and their use in the diagnosis and prognosis of human breast and ovarian cancer.

The invention also relates to the screening of this type of BRCA1 mutations in human genomic DNA, as part of clinical protocols for the diagnosis of inherited predisposition to breast and ovarian cancer.

BACKGROUND OF THE INVENTION

Breast cancer is the most common malignancy among women in the Netherlands, with a cumulative risk by age 85 of one in 11. The strongest epidemiological risk factor for the disease is a positive family history. Depending on the age of diagnosis and occurrence of bilateral disease in the index case, first degree relatives may have a relative risk of up to 10 for developing breast cancer. In the US population, 6 to 19% of women with breast cancer have at least one affected relative at the time of diagnosis [1], but not all of them are expected to be true genetic cases as the high incidence of breast cancer in the general population will inevitably cause some coincidental familial clustering. In an attempt to stratify the two classes, criteria to define truly inherited breast cancer have been proposed [2]. Such cases are characterized by early age of onset (premenopausal), excess of bilaterality, and clear paternal or maternal transmission with an autosomal dominant mode of inheritance. Approximately 5% of all cases comply with these criteria, while another 13% are classified as familial clustering [3]. Since early age of onset appears to be a hallmark of hereditary breast cancer, one may suspect that among these cases the genetic component is much higher. Indeed, up to 35% of cases diagnosed under the age of 30 are expected to be genetic [4]. No such data are available for the Dutch situation, and little or none of this has been confirmed at the molecular genetic level.

Linkage analysis of early-onset breast cancer families localized BRCA1 to the long arm of chromosome 17 [5]. Further analyses of additional families revealed that women inheriting a mutant allele of BRCA1 are also at increased risk for ovarian cancer [6, 7]. Overall, approximately 45% of all families in which breast cancer is the predominant malignancy are due to BRCA1, as are over 80% of all families with both breast and ovarian cancer [6, 8]. Female mutation carriers have been estimated to have an 87% risk to develop breast cancer before the age of 70, and 63% risk to develop ovarian cancer before the age [7]. However, significant evidence for ovarian cancer risk heterogeneity was obtained, indicating the existence of at least two classed of BRCA1 mutations; one conferring a high risk to both breast and ovarian cancer, and one conferring a high risk to breast cancer, but only a moderate risk to ovarian cancer, with the former comprising approximately 26% of all BRCA1 mutations [9]. The gene frequency of BRCA1 has been estimated to be 1 in 833 women [10]. This would imply that 1.7% of all breast cancer patients diagnosed between age 20 and 70 are carrier of such a mutation.

The gene structure of BRCA1 was found to consist of 22 coding exons spanning >80 kb of genomic DNA [11], and encoding a 7.8 kb transcript [12]. An unusually large exon 11 of 3.4 kb comprises 61% of the coding domain. Over 900 mutations in BRCA1 have been published to date and compiled into an electronically accessible database [13]. Several characteristics stand out [14]. First, they are nearly ubiquitously distributed over the gene. Second, >85% of the mutations in the database lead to premature termination of protein translation. These include basepair substitutions leading to a stop codon, small insertions and deletions (of 1 to 40 basepairs) leading to a frame-shift, or splice-site mutations leading to deletions of complete exons and frame shifts. That these changes presumably inactivate gene function is supported by the finding that the great majority of breast and ovarian tumors that develop in BRCA1 mutation carriers show loss of the wildtype allele [15]. The relevance in terms of cancer predisposition of the missense mutations remains a matter of debate. Some of them appear rare polymorphic variants, as they are also observed in control samples. Others seem to affect critical residues, such as the cysteines in the amino-terminal ring finger domain [12], which are conserved in the mouse Brca1 sequence [16]. Third, a number of mutations have been found repeatedly, reducing the number of distinct mutations to about 150. Two of these, the 185delAG mutation and the 5382insC mutation, each represent approximately 11% of all mutations thus far reported [14]. Reconstruction of the haplotypes bearing some of the most common mutations has provided strong evidence that they have either a single or a few common ancestors and may have been present in the population already for several centuries [17-19]. Consequently, the incidence of specific mutations is strongly dependent on the population from which the breast cancer families were ascertained. Thus the 185delAG mutation was picked up mainly in families of Ashkenazi-Jewish origin [20]. The extent of the founder-effect was highlighted by the finding that approximately 1% of all Ashkenazi Jews (i.e. regardless of a positive breast cancer family history) are carrying this mutation [21,22], 8 times that of the incidence of all mutations together in the general population [10]. Specific mutations have also been recurrently detected in breast cancer families of Swedish, British, Italian, and Austrian origin [18, 23-26].

Despite the vast number of BRCA1 gene changes detected to date, there remains a discrepancy between the proportion of BRCA1 mutations predicted by linkage studies [6,8], and the actual prevalence established by mutation analysis, among breast cancer families derived from a variety of ethnic backgrounds [27-31]. In general, this is explained in two ways: either a substantial number of mutations have been missed by the applied mutation screening methodology, or the genetic heterogeneity of hereditary breast cancer is significantly greater than hitherto expected.

Relatively little information of predictive value can be gleaned from the existing data. In one set of 35 kindreds with proven BRCA1 mutations from the United Kingdom, the ovarian cancer risk heterogeneity as predicted from linkage studies could be confirmed [25]. Mutations occurring before codon 1435 conferred a significantly higher ovarian cancer risk than those occurring after this point. While this is consistent with earlier predictions based on linkage analysis [9], the current mutation distribution is at odds with the predicted lower frequency of these alleles. In addition, the expressivity of BRCA1 displays considerable inter-family variability. For example, the 185delAG mutation was detected in families with early-onset breast cancer and ovarian cancer, or late-onset breast cancer without ovarian cancer [32]. Clearly, other factors influence the expression of the phenotype, and some of those might be genetic, others environmental. Of note, BRCA1 carriers who have a rare allele at the HRAS1 minisatellite locus were recently shown to be at a 2.8-fold increased risk for ovarian cancer relative to those carriers who had common alleles at HRAS1 [33]. However, a firm establishment of the full spectrum of BRCA1 gene changes in the population is pivotal for a more formal analysis of this matter.

An intriguing feature of BRCA1, and unexpected in the light of Knudson's two-hit inactivation theorem for tumor suppressor genes, is that somatically acquired mutations are extremely rare in ovarian tumors [34-38] and have in fact not yet been detected in 135 breast tumors [39-40]. This might indicate that inactivation of BRCA1 is not selected for during tumorigenesis of the non-inherited form of breast cancer. BRCA1 expression might be critical only during certain stages of tissue development, e.g., during puberty when the breast undergoes its final differentiation into a potential milk-producing gland [39]. However, others have argued that the mechanism of inactivation might be different from that seen in inherited cases [41].

SUMMARY OF THE INVENTION

The present invention now reveals that the unusual high concentration of Alu-elements in the BRCA1 gene intronic regions [11] favors the induction of large genomic deletions and inversions in a situation of increased genomic instability although other mechanisms leading to these mutations may also play significant roles. The present invention thus provides a diagnostic test kit (and means and methods) for determining mutations, especially deletions of relatively large stretches of nucleotides in genes associated with hereditary types of cancer, in particular such mutations (deletions of relatively large stretches of nucleotides) in the BRCA1 gene. Such mutations are difficult, if not impossible, to detect by the currently PCR-based approach (if their occurrence or the site thereof is unknown) using genomic DNA as template, which has been most widely applied to establish the current mutation spectrum of BRCA1.

The present invention thus provides a diagnostic test kit for detecting the presence of or predisposition for e.g. breast cancer, whereby a means is provided for detecting a deletion of a stretch of nucleotides from a BRCA 1 gene in a sample. Now that it is known that such mutations occur, it is within the skill of the art to arrive at means to determine the presence of these mutations, either the ones disclosed herein or similar mutations. Such means may include hybridization of a probe flanking both sides of the deletion, or using two probes on either side of the deletion and amplifying the stretch in between, another way may be lack of hybridization, when using a probe hybridizing to a deleted part, etc. Yet another way may be lack of amplification between one or more sets of primers targeted at or near a deleted region. This already implicates that typically multiplex PCR approaches are very suitable. Also exon-connection PCR is a very suitable approach for use in the present invention. The techniques mentioned above are well known in the art and need no further explanation. Since mutations as disclosed herein may occur in one allele only, quantitative methods are often preferable. It is of course clear that the diagnostic test kit should provide all other necessary means for determining the presence or absence of the mutations, such as buffers, detection means (possibly labels or markers), etc. A convenient diagnostic test kit according to the invention apart from amplification methods such as PCR, NASBA and the like is a diagnostic test kit whereby the means comprise the necessary elements for southern blotting. The deletions to be detected are typically relatively large stretches of nucleotides, particularly of a size which when subjected to PCR or similar amplification techniques would not be amplified under normal reaction conditions because of their length. Typically the deletion comprises one or more exons of the BRCA1 gene or a frameshift and/or a termination codon. An exemplified deletion that is a good marker for the predisposition for cancer is the deletion which comprises at least a major part of exon 22.

Another exemplified deletion that is a good marker for the predisposition for cancer is the deletion which comprises at least a major part of nucleotides 1396-1662.

Another exemplified deletion that is a good marker for the predisposition for cancer is the deletion which comprises at least a major part of exons 13-16.

Another exemplified deletion that is a good marker for the predisposition for cancer is the deletion which comprises at least a major part of exon 13.

An exemplified deletion that is a good marker for the predisposition for cancer is the deletion which comprises a stretch of nucleotides between two ALU-elements. This kind of deletion ties in very nicely with a suggested mechanism of the origin of these mutations and the same may also be found in other genes involved in cancer and having many of these elements.

Thus the invention further provides a probe for use in a diagnostic test kit according to invention comprising a nucleic acid sequence which is a fusion of two (complementary sequences of) ALU elements, in particular of the BRCA1 gene. In general the invention thus provides a probe for use in a diagnostic test kit according to the invention, which is a fusion product of two sequences adjacent to the site of a deletion of a stretch of nucleotides.

Also provided is a method for determining the presence in a sample of a nucleic acid derived from a BRCA1 gene having a deletion of a stretch of nucleotides, comprising contacting said sample with at least one probe which alone or together with other means is capable of distinguishing between BRCA1 genes having said deletion and BRCA1 genes not having said deletion, allowing for possible hybridization between said probe and said nucleic acid and identifying the hybridization product.

Specific embodiments of the invention will be explained in detail below.

DETAILED DESCRIPTION OF THE INVENTION

The present invention in one of its embodiments, which has been described in detail in the experimental part provides a description and detection in human genomic DNA of large genomic deletions in BRCA1. In addition, the invention shows involvement of the Alu-repeat elements, present at high frequency in the intronic regions of BRCA1 [11], in generating a number of these deletions. The invention also contemplates the frequency of these deletions in the Dutch population, and their descendance from a common ancestor.

Figure 1:
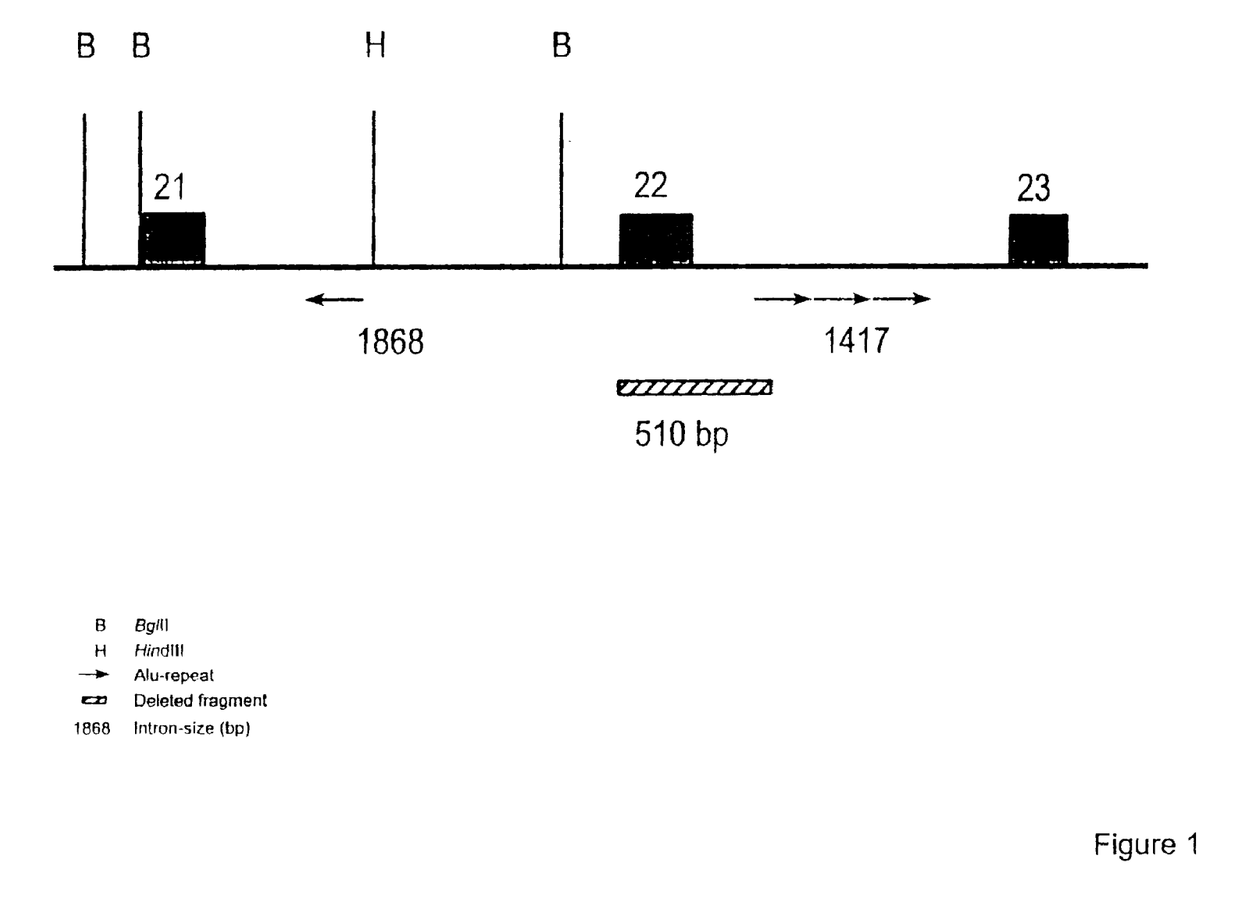
Figure 2:
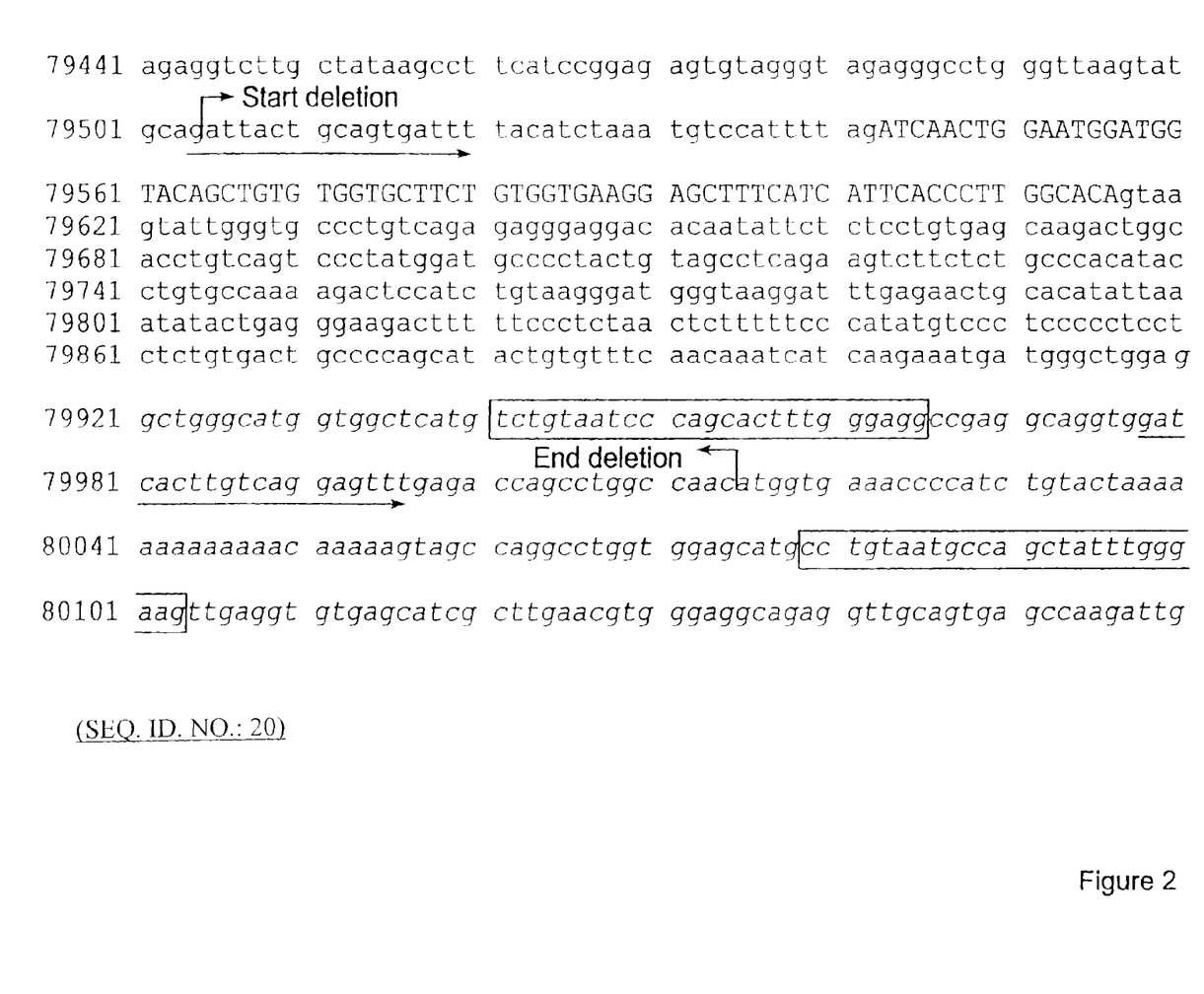

We have found that the mutation spectrum of BRCA1 as resolved up to this point [13,42] has been biased by PCR-based mutation-screening methods such as SSCP, the protein truncation test (PTT), and direct sequencing, using genomic DNA as template. We describe as examples thereof two large genomic deletions, which are not detected by these approaches, and which together comprise 38% of all BRCA1 mutations found in a sample of 170 Dutch breast cancer families [43,44]. One deletion removes 510 basepairs (bp) including exon 22 (FIG. 1) and was found 8 times. The other deletion removes 3835 bp including exon 13 (FIG. 2) and was found 4 times.

The haplotypes of the 8 families with the exon 22 deletion were reconstructed by typing 3 intragenic markers (D17S855, D17S1322, D17S1323) and 2 flanking markers (THRA1 and D17S1327). These haplotypes were completely concordant for the intragenic markers in at least 7 families, and the haplotype conservation extended proximally to THRA1, and distally to D17S1327, in at least 5 families, to comprise a genetic region of approximately 2 cM. The haplotypes of the 4 families with the exon 13 deletion were reconstructed in a similar way. These haplotypes were completely concordant for the intragenic markers in at least 2 families, and the haplotype conservation extended proximally to THRA1, and distally to D17S1327, in all 4 families, to comprise a genetic region of approximately 2 cM.

Molecular characterization of the deletions revealed that the exon 22 deletion starts in intron 21 and ends within the most upstream copy of three head-to-tail arranged Alu-elements in intron 22. A 17-bp imperfect homology to the intron 22 Alu-element was found at the 5' deletion breakpoint (FIG. 3) The 3' breakpoint is closely flanked on either side by two 25-bp sequences strongly homologous to the Alu core-sequence implied to stimulate recombination [45].

Figure 4:
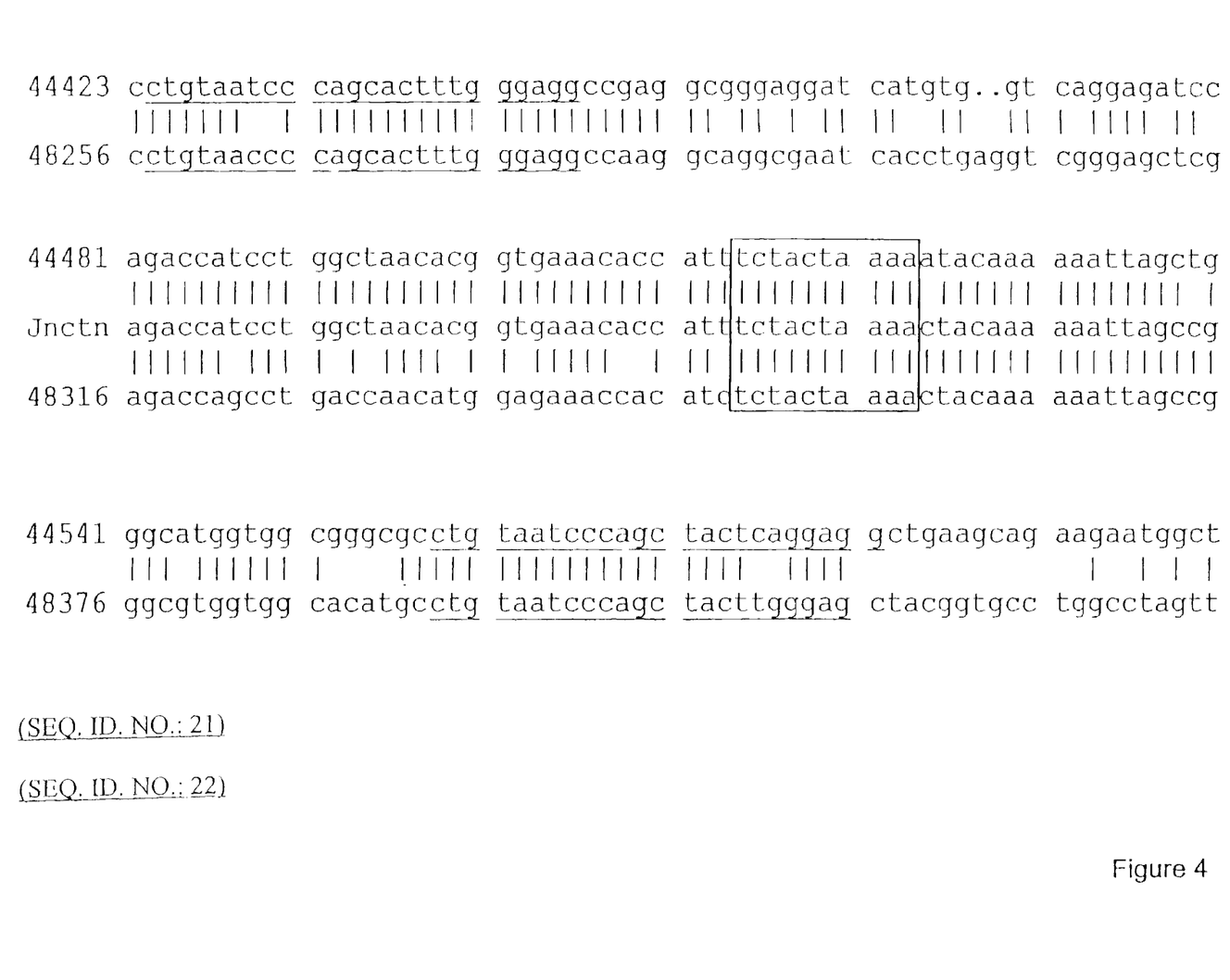
FIG. 4. Aligned sequences of intronic regions flanking exon 13 (SEQ. ID. NOS.: 21 and 22), and of the deletion-junction fragment (Jnctn) (SEQ. ID. NO.: 23). The upper sequence of each alignment corresponds to intron 12 sequences (SEQ. ID. NO.: 21), the lower sequence intron 13 sequences (SEQ. ID. NO.: 22). The numbers refer to the genomic sequence of BRCA1 (Genbank accession nr. L78833). The boxed sequence indicates the 10 bp where the recombination took place that led to the deletion of 3835 bp. The intron 12 sequence depicted here represents the first 180 bp of an Alu-element. The intron 12 region 44481-44551 shares an 85% identity with the intron 13 region 48316-48386. The underlined sequences are imperfect copies of a common 26-bp core sequence involved in recombinations leading to gene rearrangements in the LDLR gene [45].

The exon 13 deletion starts in intron 12 in an Alu-element (112 bp from the 5' end) and ends in intron 13 in a region which shares very high homology to this element (FIG. 4). Both the 5' and the 3' breakpoint are closely flanked on either side by sequences strongly homologous to the 26-bp Alu core-sequence implied to stimulate recombination [45].

The current invention facilitates the design of PCR-based strategies (now that the presence of this kind of mutations is known) to identify the heterozygous presence of the deletions in human genomic DNA. Oligonucleotide primers can be designed so to immediately flank the deletion breakpoints, and allow the specific amplification of a deletion-junction fragment as a diagnostic endpoint. Given the size of the deletions, the wildtype BRCA1 genomic sequence would remain refractory to PCR-amplification under most standard reaction conditions. PCR-based diagnosis is an essential requirement to scale up throughput in the screening for these mutations.

The current invention also pertains to the molecular mechanism which may have generated the genomic deletions in the BRCA1 gene, especially since this needs to be viewed in a broader sense in that the same kind of phenomenon may be picked up in other genes or in the same gene, but not having anything to do with the inheriting kind of cancer.

The current invention thus also pertains to the role of BRCA1 mutations in non-inherited or sporadic breast cancer.

EXAMPLES

The exon 22 deletion was revealed by Southern blot analysis of genomic DNA digested with either HindIII or BglII. As probe we used p1424, which contains ~1-kb cDNA-derived segment from exons 14-24. A carrier of the exon 22 deletion shows aberrant bands of 9.3 kb in the HindIII digest and of 6.7 kb in the BglII digest.

The exon 13 deletion was revealed by Southern blot analysis of genomic DNA digested with either HindIII or BglII. As probes we used either p11 or p1424, which contain ~1-kb cDNA-derived segments from exon 11 and exons 14-24, respectively. A carrier of the exon 13 deletion shows an aberrant band of 6.4 kb in the HindIII pattern obtained with probe p1424 and of 14 kb in the BglII pattern obtained with probe p11.

Figure 3:
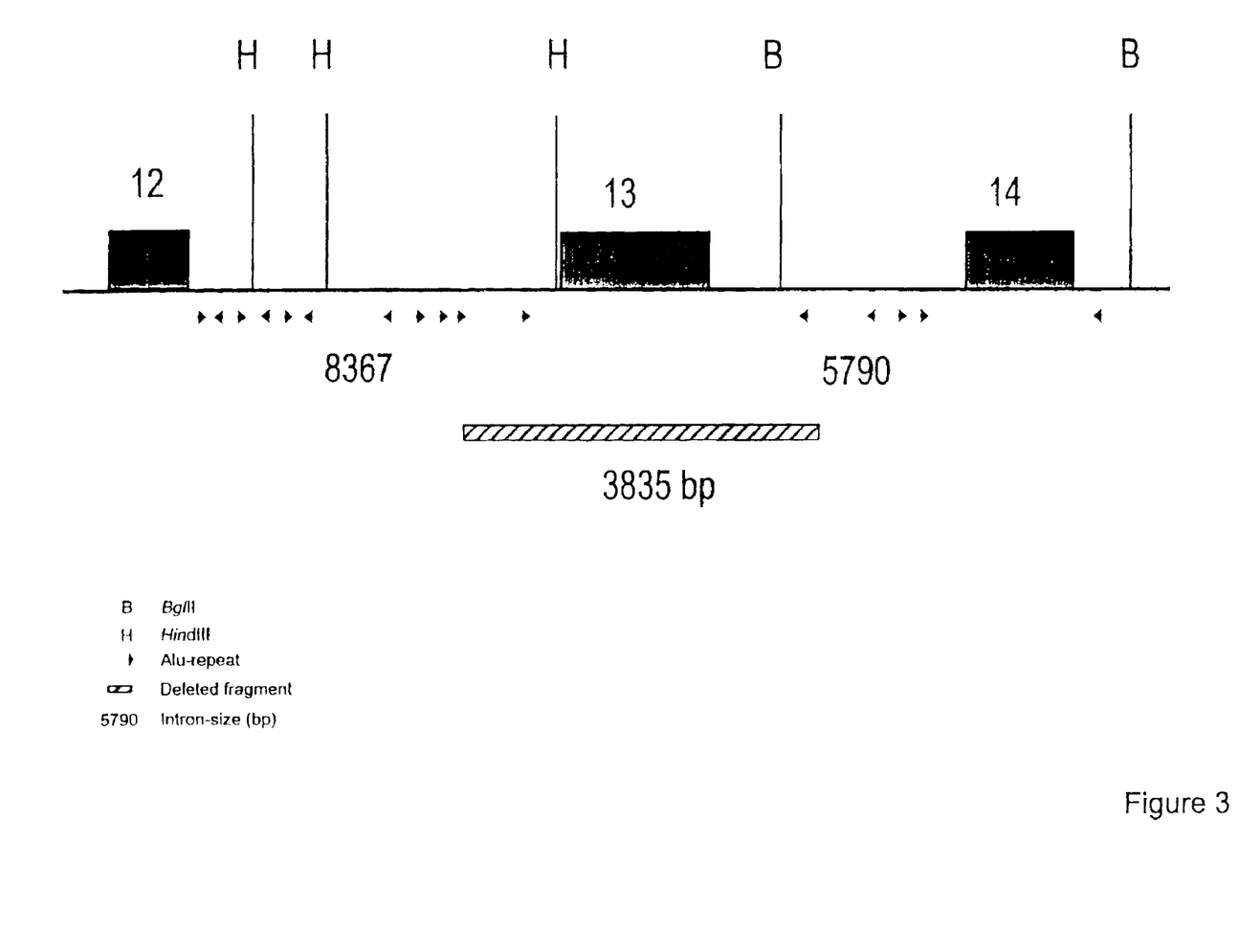

To further characterize these deletions, we used intronic amplimers to obtain PCR-products from genomic DNA, specifically containing the deletion-junction fragment. Amplimers flanking exon 22 generated an aberrant genomic fragment of 1.4 kb in DNA samples carrying the exon 22 deletion, which turned out to contain a 510-bp deletion relative to the wildtype sequence (FIG. 3). The deletion affecting exon 22 removes the bases 79505-80014 (510 bp) as listed in the genomic sequence of BRCA1 (Genbank accession nr. L78833). As a result, 74 basepairs, corresponding to exon 22, are missing in the Processed mRNA-transcript (bases 79543-79615 in Genbank accession nr. L78833).

Amplimers flanking exon 13 generated an aberrant genomic fragment of 2.7 kb in DNA samples carrying the exon 13 deletion, which turned out to contain a 3835 bp deletion relative to the wildtype sequence (FIG. 4). The deletion affecting exon 13 removes the bases 44514-48348 (3835 basepairs) as listed in the genomic sequence of BRCA1 (Genbank accession nr. L78833). As a result, 172 basepairs, corresponding to exon 13, are missing in the processed mRNA-transcript (nucleotides 46156-46327 in Genbank accession nr. L78833).

We examined 142 breast cancer families in which thusfar no BRCA1 or BRCA2 mutation had been found (refs. 43,44 and our unpublished results) for the presence of the exon 13 and exon 22 deletions. They were found in 4 and 8 families, respectively. Together with previous mutation screening results, using PTT and direct sequencing [44], these deletions thus comprise 12/32 (38%) of all families in which a BRCA1 mutation has been detected to date. Three intragenic and 2 flanking markers were used to reconstruct the disease haplotype for each of the research families carrying either the 510-bp or 3.8-kb deletion. Strong conservation of allele-lengths was observed at the intragenic loci among the haplotypes carrying the same deletion, in agreement with their descent from a common ancestor.

The haplotype in the Dutch population that carries the 510-bp deletion around exon 22 is characterized by a 155-bp allele at the microsatellite marker D17S855 in intron 20, a 122-bp allele at microsatellite marker D17S1322 in intron 19, and a 151-bp allele at microsatellite marker D17S 1323 in intron 12. The haplotype in the Dutch population that carries the 3835-bp deletion around exon 13 is characterized by a 151-bp allele at D17S855, a 122-bp allele at D17S1322, and a 151-bp allele at D17S1323 in intron 12. The primer sequences used to detect these alleles are: for D17S 1322: Forward (F) 5' CTAGCCTGGGCAACAAACGA 3' (SEQ. ID. NO.: 1 and Reverse (R) 5' GCAGGAAGCAGGAATG- GAAC 3' (SEQ. ID. NO.: 2); for D17S855: F 5' GGATGGC-CTTTTAGAAAGTGG 3' (SEQ. ID. NO.: 3) and R 5' ACA-CAGACTTGTCCTACTGC 3' (SEQ. ID. NO.: 4); for D17S1323: F 5' TAGGAGATGGATTATTGGTG 3' (SEQ. ID. NO.: 5) and R 5' AAGCAACTTTGCAATGAGTG 3' (SEQ. ID. NO.: 6). PCR conditions have been described elsewhere [44].

Detection of the Mutations

Isolation of genomic DNA and total RNA from freshly taken blood samples, and preparation of first-strand cDNA by reverse transcription, has been described [43].

cDNA Analysis to Detect the Exon 13 Deletion.

Exons 12-24 were amplified from first-strand cDNA products obtained by reverse transcription using the following primers for the first PCR: F 5' TCACAGTGCAGTGAATTG-GAAG 3' (SEQ. ID. NO.: 7) and R 5' GTAGCCAGGACAG-TAGAAGGACTG 3' (SEQ. ID. NO.: 8). The obtained PCR-products were used as template for a second PCR of exons 12-24 using nested primers (F 5' GAAGAAAGAG-GAACGGGCTTGG 3' (SEQ. ID. NO.: 9) and R 5' GGC-CACTTTGTAAGCTCATTC 3' (SEQ. ID. NO.: 10)). PCR conditions were as described previously [43]. Five µl of the final PCR products are analysed on a 1% agarose gel.

cDNA Analysis to Detect the Exon 22 Deletion.

Exons 12-24 were amplified from first-strand cDNA products obtained by reverse transcription using the following primers for the first PCR: F 5'TCACAGTGCAGTGAATTG-GAAG 3' (SEQ. ID. NO.: 7) and R 5' GTAGCCAGGACAG-TAGAAGGACTG 3' (SEQ. ID. NO.: 8). The obtained PCR-products were used as template for a second PCR of exons 20-24 using nested primers (F 5' AACCACCAAGGTC-CAAAGC 3' (SEQ. ID. NO.: 11) and R 5' GTAGCCAGGA-CAGTAGAAGGACTG 3' (SEQ. ID. NO.: 12)). PCR conditions were as described previously [43]. Five µl of the final PCR products are analysed on a 1% agarose gel.

Genomic PCR of the 3835-bp deletion spanning exon 13. A PCR reaction of 50 µl contains 200 ng of genomic DNA, 10 pmol primers (F 5' TAGGAGATGGATTATTGGTG 3' (SEQ. ID. NO.: 5) and R 5' TACGTGGGTTCAACTGAAGC 3' (SEQ. ID. NO.: 13)), 0.75 Units Amplitaq Taq polymerase (Perkin-Elmer-Cetus), and 5 µl of 10× ITP/BSA buffer (500 mM KCl 100 mM TRIS-HCl pH 8.4, 25 mM $MgCl_2$, 2 mg/ml BSA, 2 mM dNTPs). This mixture is heated at 94° C. for 5 minutes, followed by 35 cycles of PCR (at 94° C. for 45 seconds, at 52° C. for 1 min. and at 72° C. for 2.5 mm on a Perkin-Elmer-Cetus DNA thermal Cycler). The PCR is concluded by an incubation at 72° C. for 6 minutes. Five µl of the PCR products are analysed on a 1% agarose gel.

Genomic PCR of the 510-bp deletion spanning exon 22. A PCR reaction of 50 µl contains 300 ng of genomic DNA, 10 pmol primers (F 5' TCCCATTGAGAGGTCTTGCT 3' (SEQ. ID. NO.: 14) and R 5' ACTGTGCTACTCAAGCACCA 3' (SEQ. ID. NO.: 15)), 0.75 U Amplitaq Taq polymerase (Perkin-Elmer-Cetus), 5 µl Optiprime buffer #6 (Stratagene) and 0.1 mM dNTPs. Thermal cycles are as described for the deletion of 3.8 kb. Five µl of the PCR products are analysed on a 1.5% agarose gel.

Southern Analysis.

Five µg of genomic DNA is digested with either the restriction endonuclease BglII or HindIII. Agarose gels (0.8%) are run at 30V for 16 hr in TAE buffer (40 mM Tris-HAc pH 8.3, 1 mM EDTA). Procedures for denaturing, and transferring the separated DNA to nylon membranes (Hybond N+, Amersham) have been described [46]. As probes we used PCR-products obtained from a clone containing the complete BRCA1-cDNA, and purified by using the QIAquick PCR Purification Kit from QIAGEN. Probe-11 (p11) derives entirely from exon 11 and was obtained with the primers F 5' GAAAAAAAAGTACAACCAAATGCC 3' (SEQ. ID. NO.: 16) and R 5' AGCCCACTTCATTAGTACTGGAAC 3' (SEQ. ID. NO.: 17), and probe-1424 (p1424) contains exons 14-24 and was obtained with the primers F 5' TACCCTATAAGC-CAGAATCCAGAA 3' (SEQ. ID. NO.: 18); and R 5' GGC-CACTTTGTAAGCTCATTC 3' (SEQ. ID. NO.: 19). Purified fragments were labelled using the Megaprime DNA labelling System from Amersham according to suppliers protocols. Hybridizations were carried out at 65° C. in 125 mM $Na_2HPO_4.2H_2O$, 7% SDS, 10% PEG-6000, 1 mM EDTA. Final washing was in 45 mM NaCl, 4.5 mM Na-citrate pH 7.0, 0.1% SDS, at 65° C. for 30 minutes.

BRIEF DESCRIPTION OF THE DRAWINGS

FIG. 1. Schematic representation of the genomic deletion spanning exon 22 of BRCA1. The intronic regions are drawn to scale relative to one another, and the exonic region are drawn to scale relative to one another, but not to intronic regions. The positions of the restriction endonucleases HindIII and BglII, used in Southern blot analysis, are indicated. The arrows indicate the presence and orientation of an Alu-element.

FIG. 2. Sequence of exon 22 (uppercase) and its flanking intron-sequence (lower case) (SEQ. ID. NO.: 20). The numbers refer to the genomic sequence of BRCA1 (Genbank accession nr. L78833). Starting and ending positions of the 510-bp deletion are indicated by hooked arrows and affect positions 79505-80014. The first 241 bp of an Alu-element are depicted in italics, and the boxed sequences are imperfect copies (1 and 5 mismatches, respectively) of a common 26-bp core sequence involved in recombinations leading to gene rearrangements in the LDLR gene [45]. A stretch of 17 bp at the 5' junction of the deletion is homologous to a 19-bp stretch 37 bp upstream of the 3' deletion-breakpoint (underlined with arrows).

FIG. 3. Schematic representation of the genomic deletion spanning exon 13 of BRCA1. The intronic regions are drawn to scale relative to one another, and the exonic region are drawn to scale relative to one another, but not to intronic regions. The positions of the restriction endonucleases HindIII and BglII, used in Southern blot analysis, are indicated. The arrowheads indicate the presence and orientation of an Alu-element.

REFERENCES

1. Slattery M L, and Kerber R A (1993) A comprehensive evaluation of family history and breast cancer risk: the Utah Population Database. JAMA 270: 1563-1568

2. Lynch, H. T., Marcus, J. M., Watson, P., Conway, T., Fitzsimmons, M. L. & Lynch, J. F. (1989) in Genetic epidemiology of cancer (eds Lynch, H. T. & Hirayama, T.) p. 289-332, CRC Press, Inc, Boca Raton, Fla.
3. Lynch H T, Albano W A, Heieck J J, Mulcahy G M, Lynch J F, Layton M A, and Danes B S (1984) Genetics, Biomarkers, and the control of breast cancer: a review. Cancer Genet. Cytogenet. 13: 43-92
4. Claus E, Risch N, and Douglas W (1991) Genetic analysis of breast cancer in the cancer and steroid hormone study. Am. J. Hum. Genet. 48: 232-242
5. Hall J, Lee M, Newman B, Morrow J, Anderson L, Huey B, and King M (1990) Linkage of early-onset familial breast cancer to chromosome 17q21. Science 250: 1684-1689
6. Easton D, Bishop D, Ford D, Crockford G, and the Breast Cancer Linkage Consortium (1993) Genetic linkage analysis in familial breast and ovarian cancer: Results from 214 families. Am. J. Hum. Genet. 52: 678-701
7. Ford D, Easton D, Bishop D, Narod S, Goldgar D, and the Breast Cancer Linkage Consortium (1994) Risks of cancer in BRCA1-mutation carriers. Lancet 343: 692-695
8. Narod S, Ford D, Devilee P, Barkardottir R, Lynch H, Smith S, Ponder B, Weber B, Garber J, Birch J, Cornelis R, Kelsell D, Spurr N, Smyth E, Haites N, Sobol H, Bignon Y, Chang-Claude J, Hamann U, Lindblom A, Borg A, Piver M, Gallion H, Struewing J, Whittemore A, Tonin P, Goldgar D, Easton D, and the Breast Cancer Linkage Consortium (1995) An evaluation of genetic heterogeneity in 145 breast-ovarian cancer families. Am J Hum Genet 56: 254-264
9. Easton D, Ford D, Bishop D, and the Breast Cancer Linkage Consortium (1995) Breast and ovarian cancer incidence in BRCA1-mutation carriers. Am. J. Hum. Genet. 56: 265-271
10. Ford D, Easton D, and Peto J (1995) Estimates of the gene frequency of BRCA1 and its contribution to breast and ovarian cancer incidence. Am. J. Hum. Genet. 57: 1457-1462
11. Smith T M, Lee M K, Szabo C I, Jerome N, Mceuen M, Taylor M, Hood L, and King M C (1996) Complete genomic sequence and analysis of 117 kb of human DNA containing the gene BRCA1. Genome Research 6: 1029-1049
12. Miki Y, Swensen J, Shattuck-Eidens D, Futreal P, Harshman K, Tavtigian S, Liu Q, Cochran C, Bennett L, Ding W, Bell R, Rosenthal J, Hussey C, Tran T, McClure M, Frye C, Hattier T, Phelps R, Haugen-Strano A, Katcher H, Yakumo K, Gholami Z, Shaffer D, Stone S, Bayer S, Wray C, Bogden R, Dayananth P, Ward J, Tonin P, Narod S, Bristow P, Norris F, Meera Khan P, Morrison P, Rosteck P, Lai M, Barrett J, Lewis C, Neuhausen S, Cannon-Albright L, Goldgar R, Kamb A, Wiseman R, and Skolnick M (1994) A strong candidate for the breast and ovarian cancer susceptibility gene BRCA1. Science 266: 66-71
13. Breast Cancer Information Core (1997) http://www.nhgri.nih.gov/Intramural_research/Lab_transfer/Bic/
14. Couch F J, Weber B L, Borresen A L, Brody L, Casey G, Devilee P, Fitzgerald M, Friend S, Gayther S, Goldgar D, Murphy P, Szabo C, Weber B, Wiseman R, Anderson T, Durocher F, Ganguly A, King M C, Lenoir G, Narod S, Olopade O, Plummer S, Ponder B, Serova O, Simard J, Stratton M, and Warren B (1996) Mutations and polymorphisms in the familial early onset breast cancer (BRCA1) gene. Hum Mutat 8: 8-18
15. Cornelis R, Neuhausen S L, Johansson O, Arason A, Kelsell D, Ponder B A J, Tonin P, Hamann U, Lindblom A, Lalle P, Longy M, Olh E, Scherneck S, Bignon Y, Sobol H, Chang-Claude J, Larsson C, Spurr N, Borg A, Barkardottir R B, Narod S, Devilee P, and the Breast Cancer Linkage Consortium (1995) High allele loss rates at 17q12-q21 in breast and ovarian tumors from BRCA1-linked families. Genes Chrom. Cancer 13: 203-210
16. Sharan S, Wims M, and Bradley A (1995) Murine Brcal: Sequence and significance for human missense mutations. Hum. Mol. Genet. 4: 2275-2278
17. Simard J, Tonin P, Durocher F, Morgan K, Rommens J, Gingras S, Samson C, Leblanc J, Belanger C, Dion F, Liu Q, Skolnick M, Goldgar D, Shattuck-Eidens D, Labrie F, and Narod S (1994) Common origins of BRCA1 mutations in Canadian breast and ovarian cancer families. Nature Genet. 8: 392-398
18. Johannsson O, Ostermeyer E A, Hkansson S, Friedman L S, Johansson U, Sellberg C, Brondum-Nielsen K, Sele V, Olsson H, King M C, and Borg (1996) Founding BRCA1 mutations in hereditary breast and ovarian cancer in southern Sweden. Am. J. Hum. Genet. 58: 441-450
19. Neuhausen S L, Mazoyer S, Friedman L, Stratton M, Offit K, Caligo A, Tomlinson G, Cannon-Albright L, Bishop T, Kelsell D, Solomon E, Weber B, Couch F, Struewing J, Tonin P, Durocher F, Narod S, Skolnick M H, Lenoir G, Serova O, Ponder B A J, Stoppa-Lyonnet D, Easton D, King M-C, and Goldgar D E (1996) Haplotype and phenotype analysis of six recurrent BRCA1 mutations in 61 families: results of an international study. Am. J. Hum. Genet. 58: 271-280
20. Tonin P, Serova O, Lenoir G, Lynch H, Durocher F, Simard J, Morgan K, and Narod S (1995) BRCA1 mutations in Ashkenazi Jewish women. Am. J. Hum. Genet. 57: 189
21. truewing J, Abeliovich D, Peretz T, Avishai N, Kaback M, Collins F, and Brody L (1995) The carrier frequency of the BRCA1 185delAG mutation is approximately 1 percent in Ashkenazi Jewish individuals. Nature Genet. 11: 198-200
22. oa B B, Boyd A A, Volcik K, and Richards C S (1996) Ashkenazi Jewish population frequencies for common mutations in BRCA1 and BRCA2. Nature Genet. 14: 185-187
23. hattuck-Eidens D, McClure M, Simard J, Labrie F, Narod S, Couch F, Hoskins K, Weber B, Castilla L, Erdos M, Brody L, Friedman L, Ostermeyer E, Szabo C, King M, Jhanwar S, Offit K, Norton L, Gilewski T, Lubin M, Osborne M, Black D, Boyd M, Steel M, Ingles S, Haile R, Lindblom A, Olsson H, Borg A, Bishop T, Solomon E, Radice P, Spatti G, Gayther S, Ponder B, Warren W, Stratton M, Liu Q, Fujimura F, Lewis C, Skolnick M, and Goldgar D (1995) A collaborative survey of 80 mutations in the BRCA1 breast and ovarian cancer susceptibility gene: Implications for presymptomatic testing and screening. JAMA 273: 535-541
24. agner T M U, Moslinger R, Zielinski C, Scheiner O, and Breiteneder H (1996) New austrian mutation in BRCA1 gene detected in three unrelated HBOC families. Lancet 347: 1263
25. ayther S A, Warren W, Mazoyer S, Russell P A, Harrington P A, Chiano M, Seal S, Hamoudi R, Van Rensburg E J, Dunning A M, Love R, Evans G, Easton D, Clayton D, Stratton M R, and Ponder B A J (1995) Germline mutations of the BRCA 1 gene in breast and ovarian cancer families provide evidence for a genotype-phenotype correlation. Nature Genet. 11: 428-433
26. aligo M A, Ghimenti C, Cipollini G, Ricci S, Brunetti I, Marchetti V, Olsen R, Neuhausen S, Shattuckeidens D, Conte P F, Skolnick M H, and Bevilacqua G (1996)

BRCA1 germline mutational spectrum in Italian families from Tuscany: a high frequency of novel mutations. Oncogene 13: 1483-1488
27. Castilla L, Couch F, Erdos M, Hoskins K, Calzone K, Garber J, Boyd J, Lubin M, Deshano M, Brody L, Collins F, and Weber B (1994) Mutations in the BRCA1 gene in families with early-onset breast and ovarian cancer. Nature Genet. 8: 387-391
28. Inoue R, Fukutomi T, Ushijima T, Matsumoto Y, Sugimura T, and Nagao M (1995) Germline mutation of BRCA1 in Japanese breast cancer families. Cancer Res. 55: 3521-3524
29. Durocher F, Tonin P, Shattuck-Eidens D, Skolnick M, Narod S A, and Simard J (1996) Mutation analysis of the BRCA1 gene in 23 families with cases of cancer of the breast, ovary, and multiple other sites. Journal Of Medical Genetics 33: 814-819
30. Xu C F, Chambers J A, Nicolai H, Brown M A, Hujeirat Y, Mohammed S, Hodgson S, Kelsell D P, Spurr N K, Bishop D T, and Solomon E (1997) Mutations and alternative splicing of the BRCA1 gene in UK breast/ovarian cancer families. Genes Chromosomes And Cancer 18: 102-110
31. Hamann U, Brauch H, Garvin A M, Bastert G, and Scott R J (1997) German family study on hereditary breast and/or ovarian cancer: germline mutation analysis of the BRCA1 gene. Genes Chromosomes And Cancer 18: 126-132
32. Friedman L, Szabo C, Ostermeyer E, Dowd P, Butler L, Park T, Lee M, Goode E, Rowell S, and King M (1995) Novel inherited mutations and variable expressivity of BRCA1 alleles, including the founder mutation 185delAG in Ashkenazi Jewish families. Am. J. Hum. Genet. 57: 1284-1297
33. Phelan C M, Rebbeck T R, Weber B L, Devilee P, Ruttledge M H, Lynch H T, Lenoir G M, Stratton M R, Easton D F, Ponder B A J, Cannon-Albright L, Larsson C, Goldgar D E, and Narod S A (1996) Ovarian cancer risk in BRCA1 carriers is modified by the HRAS1 variable number of tandem repeat (VNTR) locus. Nature Genet. 12: 309-311
34. Hosking L, Trowsdale J, Nicolai H, Solomon E, Foulkes W, Stamp G, Signer E, and Jeffreys A (1995) A somatic BRCA1 mutation in an ovarian tumour. Nature Genet. 9: 343-344
35. Merajver S, Pham T, Caduff R, Chen M, Poy E, Cooney K, Weber B, Collins F, Johnston C, and Frank T (1995) Somatic mutations in the BRCA1 gene in sporadic ovarian tumours. Nature Genet. 9: 439-443
36. Takahashi H, Behbakht K, McGovern P, Chiu H, Couch F, Weber B, Friedman L, King M, Furusato M, LiVoisi, V, Menzin A, Liu P, Benjamin, I, Morgan M, King S, Rebane B, Cardonick A, Mikuta J, Rubin S, and Boyd J (1995) Mutation analysis of the BRCA1 gene in ovarian cancers. Cancer Res. 55: 2998-3002
37. Matsushima M, Kobayashi K, Emi M, Saito H, Saito J, Suzumori K, and Nakamura Y (1995) Mutation analysis of the BRCA1 gene in 76 Japanese ovarian cancer patients: Four germline mutations, but no evidence of somatic mutation. Hum. Mol. Genet. 4: 1953-1956
38. Lancaster J M, Cochran C J, Brownlee H A, Evans A C, Berchuck A, Futreal P A, and Wiseman R W (1996) Detection of BRCA1 mutations in women with early onset ovarian cancer by use of the protein truncation test. J. Natl. Cancer Inst. 88: 552-554
39. Futreal P, Liu Q, Shattuck-Eidens D, Cochran C, Harshman K, Tavtigian S, Bennett L, Haugen-Strano A, Swensen J, Miki Y, Eddington K, McClure M, Frye C, Weaver-Feldhaus J, Ding W, Gholami Z, Soederkvist P, Terry L, Jhanwar S, Berchuck A, Iglehart J, Marks J, Ballinger D, Barrett J, Skolnick M, Kamb A, and Wiseman R (1994) BRCA1 mutations in primary breast and ovarian carcinomas. Science 266: 120-122
40. Katagiri T, Emi M, Ito I, Kobayashi K, Yoshimoto M, Iwase T, Kasumi F, Miki Y, Skolnick M H, and Nakamura Y (1996) Mutations in the BRCA1 gene in Japanese breast cancer patients. Hum. Mutat. 7: 334-339
41. Thompson M, Jensen R, Obermiller P, Page D, and Holt J (1995) Decreased expression of BRCA1 accelerates growth and is often present during sporadic breast cancer progression. Nature Genet. 9: 444-450
42. Stratton M R, and Wooster R (1996) Hereditary predisposition to breast cancer. Curr Opin Genet Dev 6: 93-97
43. Hogervorst F, Cornelis R, Bout M, Van Vliet M, Oosterwijk J, Olmer R, Bakker B, Klijn J, Vasen H, Meijers-Heijboer H, Menko F, Cornelisse C, Den Dunnen J, Devilee P, and Van Ommen G (1995) Rapid detection of BRCA1 mutations by the Protein Truncation Test. Nature Genet. 10: 208-212
44. Peelen T, Van Vliet M, Petrij-Bosch A, Mieremet R, Szabo C, Van den Ouwenland A M W, Hogervorst F, Brohet R, Ligtenberg M J L, Teugels E, Van der Luijt R, Van der Hout A H, Gille J J P, Pals G, Jedema I, Olmer R, Van Leeuwen I, Newman B, Plandsoen M, Van der Est M, Brink G, Hageman S, Arts P J W, Bakker M M, Willems H W, Van der Looij E, Neyns B, Bonduelle M, Jansen R, Oosterwijk J C, Sijmons R, Smeets B, Van Asperen C J, Meijers-Heijboer H, Klijn J G M, De Greve J, King M-C, Menko F H, Brunner H G, Halley D, Van Ommen G-J B, Vasen H F A, Cornelisse C J, Van 't Veer L J, De Knijff P, Bakker E, and Devilee P (1997) A high proportion of novel mutations in BRCA1 with strong founder effects among Dutch and Belgian hereditary breast and ovarian cancer families. Am J Hum Genet 60: 1044-1049
45. Rudiger N S, Gregersen N, and Kielland Brandt M C (1995) One short well conserved region of Alu-sequences is involved in human gene rearrangements and has homology with prokaryotic chi. Nucleic Acids Res 23: 256-260
46. Devilee P, Van den Broek M, Kuipers-Dijkshoorn N, Kolluri R, Meera Khan P, Pearson P, and Cornelisse C (1989) At least four different chromosomal regions are involved in loss of heterozygosity in human breast carcinoma. Genomics 5: 554-560

What is claimed is:

1. A labeled probe for detecting a deletion of a stretch of nucleotides from a BRCA1 gene, wherein said deletion consists of:
   a. exon 22,
   b. nucleotides 1396-1662,
   c. exons 13 through 16,
   d. exon 13,
   e. an exon 22 deletion that starts in intron 21 and ends in intron 22, or
   f. an exon 13 deletion that starts in intron 12 and ends in intron 13 wherein the probe is a fusion product of two nucleic acid sequences adjacent to the deletion that is capable of detecting the deletion.

2. A diagnostic test kit for detecting a predisposition for breast and ovarian cancer, comprising a labeled probe for detecting a deletion of a stretch of nucleotides from a BRCA1 gene, wherein the labeled probe consists of:
   a. a sequence specific for detecting a deletion consisting of exon 22,
   b. a sequence specific for detecting a deletion consisting of nucleotides 1396-1662,
   c. a sequence specific for detecting a deletion consisting of exons 13 through 16,
   d. a sequence specific for detecting a deletion consisting of exon 13,
   e. a sequence specific for detecting a deletion consisting of an exon 22 deletion that starts in intron 21 and ends in intron 22, or
   f. a sequence specific for detecting a deletion consisting of an exon 13 deletion that starts in intron 12 and ends in intron 13 wherein the probe is a fusion product of two nucleic acid sequences adjacent to the deletion that is capable of detecting the deletion.

3. A diagnostic test kit according to claim 2, comprising at least two of a, b, c, and d.

4. A diagnostic test kit according to claim 2, comprising at least four of a, b, c, and d.

5. A diagnostic test kit for detecting a predisposition for breast and ovarian cancer, comprising labeled probes for detecting in a sample the presence of a nucleic acid derived from a BRCA1 gene having a deletion, wherein the probes comprise at least two of the following:

a. a labeled sequence specific for either side of a deletion consisting of exon 22, b. a labeled sequence specific for either side of a deletion consisting of nucleotides 1396-1662, c. a labeled sequence specific for either side of a deletion consisting of exons 13 through 16, d. a labeled sequence specific for either side of a deletion consisting of exon 13, e. a labeled sequence specific for a deletion consisting of an exon 22 deletion that starts in intron 21 and ends in intron 22, or f. a labeled sequence specific for a deletion consisting of an exon 13 deletion that starts in intron 12 and ends in intron 13.

6. A diagnostic test kit according to claim 2, comprising at least three of a, b, c, and d.

7. A diagnostic test kit according to claim 2, comprising at least four of a, b, c, and d.

* * * * *

UNITED STATES PATENT AND TRADEMARK OFFICE
CERTIFICATE OF CORRECTION

PATENT NO.        : 7,507,800 B2
APPLICATION NO.   : 10/654382
DATED             : March 24, 2009
INVENTOR(S)       : van Ommen et al.

It is certified that error appears in the above-identified patent and that said Letters Patent is hereby corrected as shown below:

Column 2, line 8:

Now reads:    "at least two classed"

Should read:    -- at least two classes --

Column 7, line 46:

Now reads:    "at 72° C. for 2.5 mm"

Should read:    -- at 72° C. for 2.5 min. --

Signed and Sealed this

Fifteenth Day of September, 2009

David J. Kappos
*Director of the United States Patent and Trademark Office*

SEQUENCE LISTING

<160> NUMBER OF SEQ ID NOS: 23

<210> SEQ ID NO 1
<211> LENGTH: 20
<212> TYPE: DNA

```
<213> ORGANISM: Artificial sequence
<220> FEATURE:
<223> OTHER INFORMATION: primer forward for D17S1322

<400> SEQUENCE: 1
ctagcctggg caacaaacga                                              20

<210> SEQ ID NO 2
<211> LENGTH: 20
<212> TYPE: DNA
<213> ORGANISM: Artificial sequence
<220> FEATURE:
<223> OTHER INFORMATION: primer reverse for D17S1322

<400> SEQUENCE: 2
gcaggaagca ggaatggaac                                              20

<210> SEQ ID NO 3
<211> LENGTH: 21
<212> TYPE: DNA
<213> ORGANISM: Artificial sequence
<220> FEATURE:
<223> OTHER INFORMATION: primer forward for D17S855

<400> SEQUENCE: 3
ggatggcctt ttagaaagtg g                                            21

<210> SEQ ID NO 4
<211> LENGTH: 20
<212> TYPE: DNA
<213> ORGANISM: Artificial sequence
<220> FEATURE:
<223> OTHER INFORMATION: primer reverse for D17S855

<400> SEQUENCE: 4
acacagactt gtcctactgc                                              20

<210> SEQ ID NO 5
<211> LENGTH: 20
<212> TYPE: DNA
<213> ORGANISM: Artificial sequence
<220> FEATURE:
<223> OTHER INFORMATION: primer forward for D17S1323

<400> SEQUENCE: 5
taggagatgg attattggtg                                              20

<210> SEQ ID NO 6
<211> LENGTH: 20
<212> TYPE: DNA
<213> ORGANISM: Artificial sequence
<220> FEATURE:
<223> OTHER INFORMATION: primer reverse for D17S1323

<400> SEQUENCE: 6
aagcaacttt gcaatgagtg                                              20

<210> SEQ ID NO 7
<211> LENGTH: 22
<212> TYPE: DNA
<213> ORGANISM: Artificial sequence
<220> FEATURE:
<223> OTHER INFORMATION: primer forward for first PCR

<400> SEQUENCE: 7
tcacagtgca gtgaattgga ag                                           22
```

<210> SEQ ID NO 8
<211> LENGTH: 24
<212> TYPE: DNA
<213> ORGANISM: artificial sequence
<220> FEATURE:
<223> OTHER INFORMATION: primer reverse for first PCR

<400> SEQUENCE: 8
gtagccagga cagtagaagg actg                                          24

<210> SEQ ID NO 9
<211> LENGTH: 22
<212> TYPE: DNA
<213> ORGANISM: artificial sequence
<220> FEATURE:
<223> OTHER INFORMATION: primer forward for second PCR

<400> SEQUENCE: 9
gaagaaagag gaacgggctt gg                                            22

<210> SEQ ID NO 10
<211> LENGTH: 21
<212> TYPE: DNA
<213> ORGANISM: artificial sequence
<220> FEATURE:
<223> OTHER INFORMATION: primer reverse for second PCR

<400> SEQUENCE: 10
ggccactttg taagctcatt c                                             21

<210> SEQ ID NO 11
<211> LENGTH: 19
<212> TYPE: DNA
<213> ORGANISM: artificial sequence
<220> FEATURE:
<223> OTHER INFORMATION: primer forward

<400> SEQUENCE: 11
aaccaccaag gtccaaagc                                                19

<210> SEQ ID NO 12
<211> LENGTH: 24
<212> TYPE: DNA
<213> ORGANISM: Artificial sequence
<220> FEATURE:
<223> OTHER INFORMATION: primer reverse

<400> SEQUENCE: 12
gtagccagga cagtagaagg actg                                          24

<210> SEQ ID NO 13
<211> LENGTH: 20
<212> TYPE: DNA
<213> ORGANISM: artificial sequence
<220> FEATURE:
<223> OTHER INFORMATION: primer reverse

<400> SEQUENCE: 13
tacgtgggtt caactgaagc                                               20

<210> SEQ ID NO 14
<211> LENGTH: 20
<212> TYPE: DNA
<213> ORGANISM: artificial sequence
<220> FEATURE:

-continued

<223> OTHER INFORMATION: primer forward

<400> SEQUENCE: 14
tcccattgag aggtcttgct                                               20

<210> SEQ ID NO 15
<211> LENGTH: 20
<212> TYPE: DNA
<213> ORGANISM: artificial sequence
<220> FEATURE:
<223> OTHER INFORMATION: primer reverse

<400> SEQUENCE: 15
actgtgctac tcaagcacca                                               20

<210> SEQ ID NO 16
<211> LENGTH: 24
<212> TYPE: DNA
<213> ORGANISM: artificial sequence
<220> FEATURE:
<223> OTHER INFORMATION: primer forward

<400> SEQUENCE: 16
gaaaaaaaag tacaaccaaa tgcc                                          24

<210> SEQ ID NO 17
<211> LENGTH: 24
<212> TYPE: DNA
<213> ORGANISM: artificial sequence
<220> FEATURE:
<223> OTHER INFORMATION: primer reverse

<400> SEQUENCE: 17
agcccacttc attagtactg gaac                                          24

<210> SEQ ID NO 18
<211> LENGTH: 24
<212> TYPE: DNA
<213> ORGANISM: artificial sequence
<220> FEATURE:
<223> OTHER INFORMATION: primer forward

<400> SEQUENCE: 18
taccctataa gccagaatcc agaa                                          24

<210> SEQ ID NO 19
<211> LENGTH: 21
<212> TYPE: DNA
<213> ORGANISM: artificial sequence
<220> FEATURE:
<223> OTHER INFORMATION: primer reverse

<400> SEQUENCE: 19
ggccactttg taagctcatt c                                             21

<210> SEQ ID NO 20
<211> LENGTH: 720
<212> TYPE: DNA
<213> ORGANISM: Homo sapiens

<400> SEQUENCE: 20
agaggtcttg ctataagcct tcatccggag agtgtagggt agagggcctg ggttaagtat    60
gcagattact gcagtgattt tacatctaaa tgtccatttt agatcaactg gaatggatgg   120
tacagctgtg tggtgcttct gtggtgaagg agctttcatc attcacccctt ggcacagtaa   180

-continued

```
gtattgggtg ccctgtcaga gagggaggac acaatattct ctcctgtgag caagactggc      240
acctgtcagt ccctatggat gcccctactg tagcctcaga agtcttctct gcccacatac      300
ctgtgccaaa agactccatc tgtaagggat gggtaaggat ttgagaactg cacatattaa      360
atatactgag ggaagacttt ttccctctaa ctctttttcc catatgtccc tccccctcct      420
ctctgtgact gccccagcat actgtgtttc aacaaatcat caagaaatga tgggctggag      480
gctgggcatg gtggctcatg tctgtaatcc cagcactttg ggaggccgag gcaggtggat      540
cacttgtcag gagtttgaga ccagcctggc caacatggtg aaaccccatc tgtactaaaa      600
aaaaaaaaac aaaaagtagc caggcctggt ggagcatgcc tgtaatgcca gctatttggg      660
aagttgaggt gtgagcatcg cttgaacgtg ggaggcagag gttgcagtga gccaagattg      720

<210> SEQ ID NO 21
<211> LENGTH: 178
<212> TYPE: DNA
<213> ORGANISM: Homo sapiens

<400> SEQUENCE: 21
cctgtaatcc cagcactttg ggaggccgag gcgggaggat catgtggtca ggagatccag       60
accatcctgg ctaacacggt gaaacaccat ttctactaaa actacaaaaa attagctggg      120
catggtggcg ggcgcctgta atcccagcta ctcaggaggc tgaagcagaa gaatggct       178

<210> SEQ ID NO 22
<211> LENGTH: 180
<212> TYPE: DNA
<213> ORGANISM: Homo sapiens

<400> SEQUENCE: 22
cctgtaaccc cagcactttg ggaggccaag gcaggcgaat cacctgaggt cgggagctcg       60
agaccagcct gaccaacatg gagaaaccac atctctacta aaactacaaa aaattagccg      120
ggcgtggtgg cacatgcctg taatcccagc tacttgggag ctacggtgcc tggcctagtt      180

<210> SEQ ID NO 23
<211> LENGTH: 60
<212> TYPE: DNA
<213> ORGANISM: Homo sapiens

<400> SEQUENCE: 23
agaccatcct ggctaacacg gtgaaacacc atttctacta aaactacaaa aaattagccg       60
```